United States Patent [19]

Doernberg et al.

[11] 3,955,421

[45] May 11, 1976

[54] PERIPHYTON SAMPLER FOR WATER QUALITY MONITORING

[75] Inventors: Robert J. Doernberg; Earl J. Huddleston; James F. Mariol, all of Cincinnati, Ohio

[73] Assignee: Design Alliance, Inc., Cincinnati, Ohio

[22] Filed: Mar. 27, 1975

[21] Appl. No.: 562,461

[52] U.S. Cl. .............................. 73/421 R; 73/421 B
[51] Int. Cl.² ......................................... G01N 1/10
[58] Field of Search .............. 73/421 R, 421 B, 425, 73/53; 206/72, 316, 455, 456

[56] References Cited
UNITED STATES PATENTS

| | | | |
|---|---|---|---|
| 3,218,744 | 11/1965 | Danner | 206/72 UX |
| 3,890,844 | 6/1975 | Gale | 73/421 R |

*Primary Examiner*—Jerry W. Myracle
*Assistant Examiner*—Joseph W. Roskos
*Attorney, Agent, or Firm*—Wood, Herron & Evans

[57] ABSTRACT

The sampler is intended to hold a plurality of microscope slides which, in use, are disposed just below the water surface. In use, the sampler holds the slides in parallel spaced relation to each other by means of a slide holder which has a pair of oppositely disposed channel-shaped side members that pivot between a slide-holding position whereat the ends of each slide project into the channel and a slide-releasing position whereat each slide can be easily grasped by its edge and removed. The slide holder is held by a wire bail and a retainer clip so that the side members cannot pivot from their slide-holding position thereby preventing the slides from falling from the holder. The bail itself is pivoted to two floatation members and shaped to dispose the slide holder at a location displaced away from the pivot axis through each floatation member thereby making the sampler capsize-proof because the slide holder will pivot to a position below the water surface even if the sampler is turned over. The floatation members are constructed so that little of the sampler is visible to passersby when floating in water.

30 Claims, 6 Drawing Figures

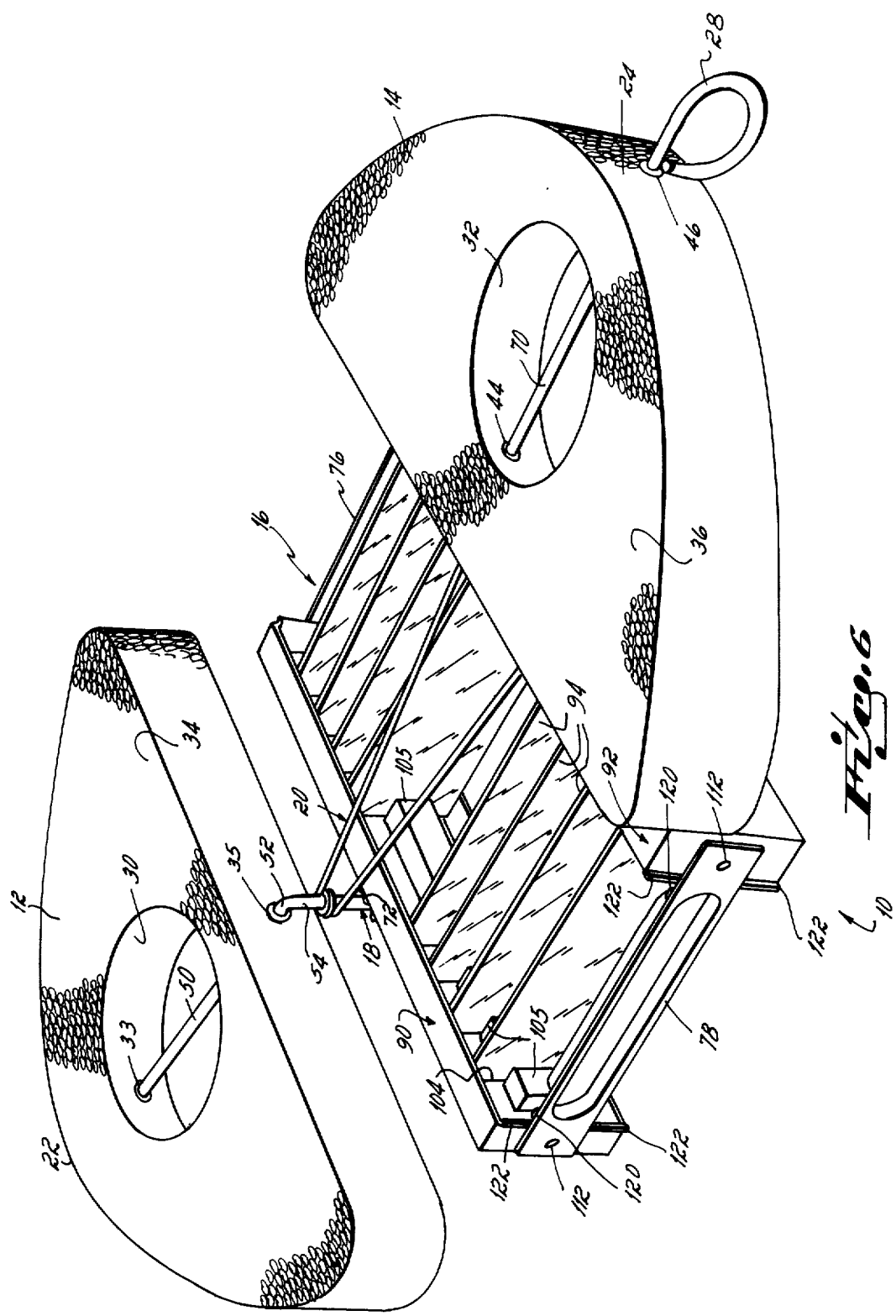

PERIPHYTON SAMPLER FOR WATER QUALITY MONITORING

BACKGROUND OF THE INVENTION

The invention relates generally to the field of water sampling and more particularly to a periphyton sampler for water quality monitoring.

For many years periphyton samplers have been used as a research tool especially by aquatic biologists. In recent years, however, with the enactment of laws relating to water quality, periphyton samplers have been used for routine evaluation as well as long-term monitoring by government biologists and others. These samplers permit investigators to monitor water quality, identify polluted water and also locate water pollution sources.

Prior art samplers generally take the form of a floating rack for holding a plurality of glass microscope slides at a position just below the surface of the water being monitored. The sampler is placed in a stream, reservoir or lake and secured by a line to some anchor so the sampler will remain substantially stationary. The sampler is left in place for approximately two weeks during which time biological growth, usually in the form of algae, appears on the slides. At the end of the two week period, the sampler and slides are removed so that the biological growth on the slides can be identified and counted. From this information, water quality can be monitored.

Prior art periphyton samplers have generally been very expensive, custom made devices. For example, one typical prior art periphyton samplers has been made of plexiglass with Styrofoam floats. This sampler required a large number of plexiglass parts which were either screwed or cemented together, thereby contributing to high assembly labor cost. The screws were generally made of brass, thereby increasing parts cost.

Another failure of typical prior art periphyton samplers is that the floats are not easily replaced and can become eroded especially where the sampler is used in bodies of water frequently having chemical spills. For example, Styrofoam floats have been known to disintegrate after having come in contact with a gasoline spill.

Capsizing is another frequently encountered problem with known periphyton samplers. Often, wave action has a tendency to turn the sampler over, thus exposing the slides to the air and direct sunlight thereby killing the biological growth on the slides. If the sampler does capsize and expose the slides during a testing period, the test results are dramatically affected thereby giving rise to unreliable water quality monitoring.

A further problem frequently occurring with prior art periphyton samplers is that of vandalism. Since the devices must be anchored in water for a period of approximately two weeks and because the floatation members cause the sampler to be easily seen, they are easily discovered and often tampered with by boatmen, swimmers and others passing by. As such, the accuracy of the tests made with known samplers is subject to question.

A further disadvantage of known periphyton samplers is the relative difficulty in inserting and removing slides from the sampler. Known samplers have had slide holders permanently attached to or supported by floatation members thereby requiring on site loading and unloading, which is time consuming, or requiring used samplers to be completely replaced by another sampler and the slides removed from the first and used sampler when it is returned to the testing laboratory. This approach is costly and inefficient.

In view of the foregoing difficulties with known periphyton samplers for water quality monitoring, it is the primary objective of the present invention to provide a periphyton sampler which is capsize-proof so that the test results from water quality monitoring will be accurate.

It is still a further objective of the invention to provide a periphyton sampler for water quality monitoring that has a low profile in use so as to make the sampler difficult to be seen by boatmen, swimmers and other passersby, thereby reducing the likelihood of vandalism.

It is still another objective of the invention to provide a periphyton sampler for water quality monitoring in which slides are quickly and easily removed and replaced.

It is yet a further objective of the invention to provide a periphyton sampler for water quality monitoring which is shaped as well as being made in part with transparent materials so that the slides, in use, will not be shaded by the sampler itself so that the effect of sunlight on biological growth on the entire surface of each slide during a test can be substantially equalized.

It is still another objective of the invention to provide a periphyton sampler for water quality monitoring which can be manufactured and assembled quickly and inexpensively.

BRIEF DESCRIPTION

The invention is predicated in part on the concept of providing a periphyton sampler for water quality monitoring which supports a plurality of glass slides or the like in a slide holder which itself is supported by a bail pivotally attached to floatation members so that the slide holder will pivot, in use, to a position below the water surface even if the sampler is overturned.

In a preferred form, the slide holder of the periphyton monitor includes two side members each being pivoted at opposite ends to end plates. The side members are generally channel-shaped in cross section with the opposed channel openings facing each other and adapted to receive the ends of each of a plurality of glass slides when the side members are disposed at their slide-holding position. A detent and lip arrangement prevents the side members from pivoting away from the slide-holding position. When the side members are forcefully pivoted to the slide-releasing position by physically overcoming the detent bias, the slides may be easily inserted or removed from the holder.

The slide holder itself is preferably supported by a metal bail member. The metal bail member is pivotally attached to two independent floatation members and is shaped to position the slide holder at the slide-holding position. The holder itself is held to the bail by oppositely disposed slots and a retainer clip. Should the sampler be turned over, the slides will not fall from slide holder and the holder will pivot to a position where it is completely submerged below the water surface thereby avoiding the problem of prolonged direct exposure of the slides to sunlight and air during a testing period. Releasing the retainer clip permits the slide holder to be removed from the bail thereby facilitating easy on site slide changing by simply changing a preloaded slide holder for the slide holder in use at the site.

The floatation members themselves are preferably made of a foam material resistant to chemical spills and shaped to present a low profile when floating in the water, thereby avoiding easy observation by swimmers, boatmen and other passersby. The buoyancy of the floatation members can be controlled by cutting a hole through the floatation material. As such, the sampler can be made so that very little of the floatation members in use extend above the water surface. The floatation members are also preferably made of a dark colored material so that the portion thereof above the waterline is less easily seen. The floatation members are also shaped so that the pivotal attachment to the bail lies along the symmetry axis through each floatation member. As such, the floatation members themselves tend to float flat on the water and wave action thereon does not tend to turn the sampler over.

The foregoing objects and advantages of the present invention will become clearer from the following detailed description of the invention taken in connection with the drawings which form a part of the original disclosure wherein:

FIG. 6 is a perspective view of the periphyton sampler.

DETAILED DESCRIPTION

Figure 1:
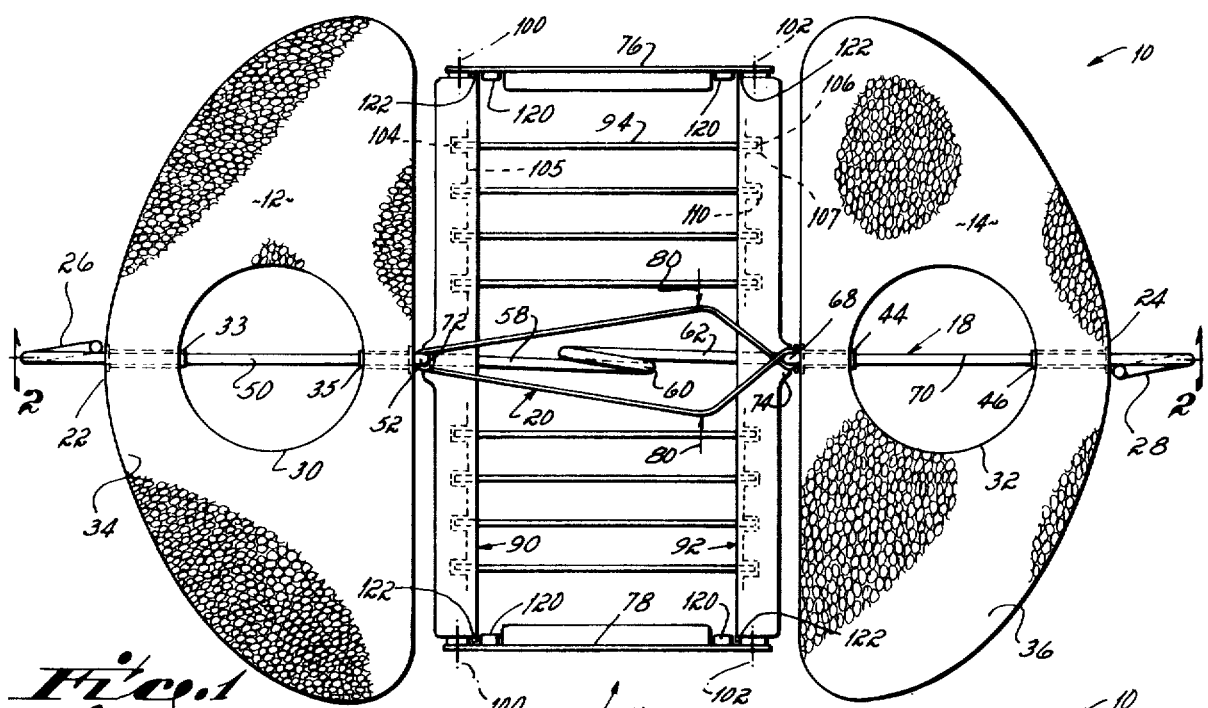
FIG. 1 is a plan view of the periphyton sampler.

Referring first to FIG. 1, the periphyton sampler, shown generally at 10, includes two floatation members 12 and 14, a slide holder shown generally at 16, a bail 18 and a retainer clip 20. The bail 18 extends through each floatation member 12 and 14 and also holds the slide holder 16 therebetween. The retainer clip 20 connects between two portions of the bail 18 to positively lock the slide holder 16 to the bail 18.

The floatation members 12 and 14 are preferably made of a polyethylene foam material with a dark coloration to reduce visability of the sampler 10 to passersby thereby reducing the likelihood of vandalism. Each floatation member 12 and 14 is generally in the shape of an isosceles triangle having a substantially uniform thickness with the triangle apex 22 for floatation member 12 being disposed away from the slide holder 16 and the triangle apex 24 of floatation member 14 also disposed away from the slide holder 16. The general triangular shape of the floatation members 12 and 14 is advantageous when the sampler is used in moving water as this shape tends to deflect flotsam and debris off of and around the sampler. The generally triangular shape also permits the sampler 10 to be moved by a line attached to either anchor ring 26 or 28 without becoming snagged or caught on floating or submerged objects against which the floatation members 12 and 14 might come in contact.

Figure 2:
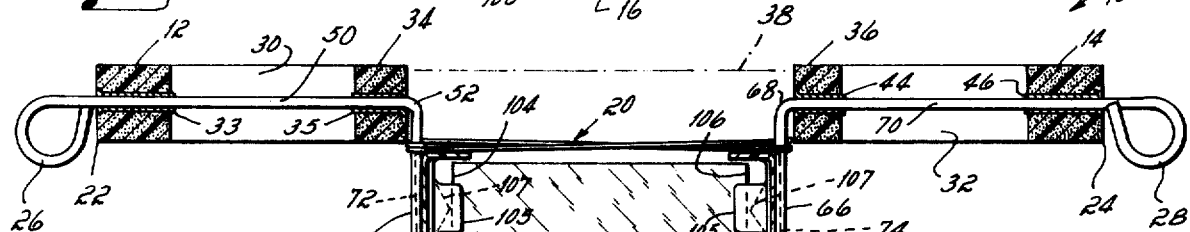
FIG. 2 is a vertical sectional view through the periphyton sampler taken along the section line 2—2 of FIG. 1.

Each floatation member 12 and 14 has a circular hole 30 and 32 respectively cut therethrough which aids in manufacture of the sampler. Also, the diameter of these holes 30 and 32 may be selected so as to reduce the total volume of the floatation members 12 and 14 so that the sampler, as best shown in FIG. 2, will float in water with the upper surface 34 and 36 of the floatation members 12 and 14 respectively being just slightly above the water surface 38. In this manner the visability of the sampler to passersby is significantly reduced because very little of the sampler itself is exposed above the water surface 38.

The shape of the floatation members 12 and 14 as well as the location of the circular holes 30 and 32 is preferably symmetric about an axis of symmetry. The axis of symmetry preferably is located along the bail 18 where it passes through the floatation members 12 and 14. By making the floatation members 12 and 14 symmetric about the bail 18, each of the floatation members 12 and 14 will float substantially level with the water surface and will make the sampler capsize-proof because the bail 18 is located along the axis of symmetry through the floatation members 12 and 14, thereby balancing the assembly.

The bail 18 which preferably is made of stainless steel wire passes through two eyelets 33 and 35 which are preferably made of nickle-chrome plated brass and aligned along the axis of the symmetry of the floatation member 12. The inner diameter of the eyelets 33 and 35 is just slightly larger than the diameter of the bail 18 thereby making the floatation member 12 freely pivotable on the bail 18. The bail 18 passes through eyelets 44 and 46 which are aligned along the axis of symmetry of floatation member 14 thereby making floatation member 14 also freely pivotable on the bail 18. Therefore, if the center of gravity of the bail 18 and the slide holder 16 is mounted thereon is disposed away from the axis of symmetry of both floatation members 12 and 14, the slide holder 16 in use will never experience prolonged direct exposure to the air and sunlight because the whole assembly will freely pivot about the symmetry axis through the floatation members 12 and 14 and come to rest below the waterline.

Referring again to FIG. 2, the bail 18 has an anchor ring 26 formed at its leftmost end. This anchor ring 26 is made after the floatation member 12 is compressed, the compression being facilitated by the hole 30, by bending the bail wire to form a loop. Disposed to the right of the anchor ring 26 is a horizontally disposed and substantially straight section shown generally at 50. This section 50 passes through both eyelets 33 and 35 and lies substantially along the axis of symmetry of floatation member 12. After passing through the eyelet 35, the bail 18 has a bend, shown generally at 52, which causes the bail to extend downwardly in a substantially vertical direction along a section shown generally at 54. The bail has another bend at 56 whereat the bail is bent so as to extend underneath the slide holder 16 along a straight section 58 which angles downwardly and rightwardly from the bend 56 until it is coiled to form a loop, as shown generally at 60. This loop 60 comprises a below water anchor point to which a line, wire, cable or the like can be attached thereby permitting the sampler to be anchored to a point below the water surface.

After extending around a loop 60, the bail 18 continues along a straight section shown generally at 62 which angles upwardly and rightwardly from the loop 60 until reaching a bend, shown generally at 64 whereat the bail wire turns vertically upwardly to form the vertical section shown generally at 66. At the upper end of section 66, the bail 18 bends to the right at 68 to form a horizontal section shown generally as 70 which passes through the eyelets 44 and 46 which are aligned along the axis of symmetry of the floatation member 14. When emerging from the apex 24, the bail 18 is coiled to form the anchor ring 28 which is formed in the same manner as ring 26.

As best viewed in FIG. 2, the sections 54 and 66 are disposed perpendicular to the axis of symmetry through both floatation members 12 and 14. These sections 54 and 56 are designed to fit into a vertically disposed slot located generally at 72 and 74 (see FIG. 1) which are located along opposite sides of the slide holder 16 midway between the opposite ends 76 and 78. As such, the slide holder 16, as viewed in FIG. 1, is designed so that approximately ½ of the slide holder 16 weight is disposed above an imaginary line drawn between the slots 72 and 74 while the other half of the slide holder 16 weight is disposed below that line thereby providing balanced contact between the slide holder 16 and the bail 18.

As viewed in FIG. 1, the retainer clip 20, which preferably is also made of stainless steel wire, extends from section 54 to section 66 of the bail 18. The clip 20 is positioned above the slide holder 16 with a portion coiled around the bail along section 54 and another portion engaging the section 66. The retainer clip 20 preferably pulls sections 54 and 66 toward each other when in its locking position to thereby secure the slide holder 16 to the bail 18. Similarly, the bends 56 and 64 prevent the slide holder 16 from moving downwardly while the slots 72 and 74 prevent movement transverse to the bail at 54 and 66. As such, so long as the retainer clip 20 remains in the locking position shown in FIG. 1 as well as FIG. 2, the slide holder 16 is securely attached to the bail 18.

By applying oppositely directed forces to the clip 20 in a direction shown generally by the arrows 80, the retainer clip 20 can be released from engagement with section 66. Once released, the clip can be swung aside to a position whereat the slide holder 16 can be disengaged from the bail 18 simply by grasping and raising the slide holder 16. As such, the sampler of the present invention permits the slide holder itself to be easily removed from the assembly without requiring that the sampler be removed from an anchor line which may be attached to any one of the rings 26, 28 or 60.

As viewed in FIG. 1, the slide holder 16 includes two substantially parallel disposed end members 76 and 78 each of which is pivotally joined to two side members, shown generally at 90 and 92. The end members 76 and 78 are respectively pivoted about the pivot axes 100 and 102. As will become clearer later, the pivotal connections with the end members 76 and 78 assist inserting and removing microscope slides 94 from the slide holder 16.

Figures 3, 4:
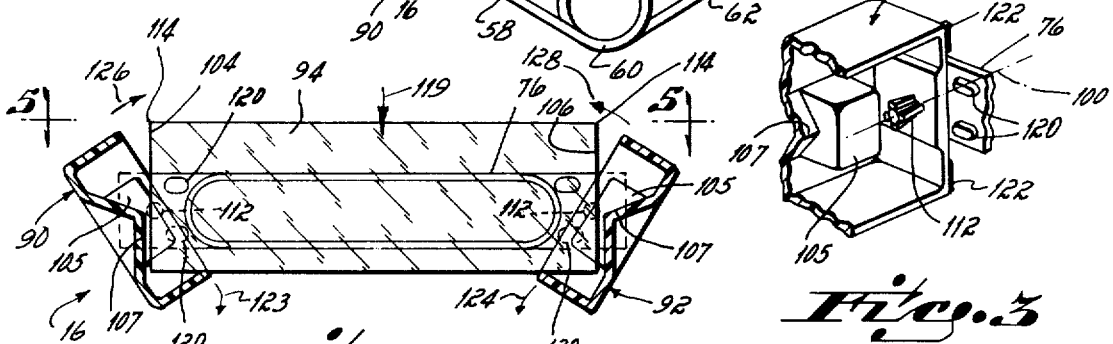
FIG. 3 is a perspective cutaway view of a portion of a side member for the slide holder.
FIG. 4 shows an end view of the slide holder with the side members positioned at their slide-releasing position.
Figure 5:
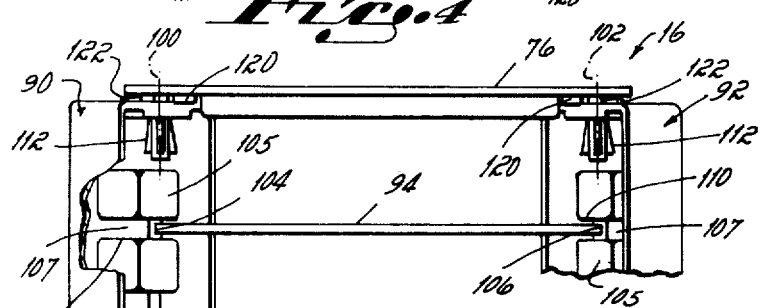
FIG. 5 is a partially cutaway view of the slide holders with the side members positioned at their slide-releasing position.

The slide holder 16 is designed to hold a plurality of microscope slides 94 each of which preferably comprise a 25 mm × 75 mm piece of clear glass although other sizes can also be used with appropriate dimension changes for other sampler parts. As will become clearer later, the slides 94 are retained is substantially parallel spaced relation at opposite ends thereof when the side members 90 and 92 are pivoted to their slide-holding position shown in FIGS. 1, 2 and 6. When the side members 90 and 92 are pivoted to their slide-releasing position as shown in FIGS. 4 and 5, each slide 94 can be easily removed.

The end members 76 and 78 as well as the side members 90 and 92 are preferably made of a transparent moldable material such as cellulose acetate butyrate. The material is preferably transparent so that each slide 94 held by the slide holder 16 will receive substantially the same amount of sunlight on every portion of the slide. In this manner, biological growth which appears on the slide during water testing will receive substantially the same amount of sunlight as any other portion of the same slide 94. Where uniformity of biological growth is not a problem, the slide holder 16 may be made of a dark colored opaque material thus tending to further reduce visibility of the sampler when in use.

As viewed in FIGS. 2–5, each side member 90 or 92 is substantially channel-shaped in cross section with the channel extending longitudinally along the length of each side member 90 or 92. The side members 90 and 92 are positioned in parallel spaced relation to each other with the distance between the side members 90 and 92 being sufficient to receive each slide 94 so that the ends 104 and 106 thereof project into the channel of each side member 92 and 94 when disposed at the slide-holding position as shown in FIG. 2. As such, a slide holder 16, once loaded with slides 94, will support each slide 94 until the side members 90 and 92 are pivoted from their slide-holding position.

The slide holder 16 also includes means for holding the side members 90 and 92 at their slide-holding position even when the holder 16 has been removed from the sampler. This is achieved by the cooperative action of the detents 120 and the lip 122. The detents 120 are located on the end members 76 and 78. The endwise projecting lip 122 extends outwardly from the ends of each side member 90 and 92 at a point adjacent the end members 76 and 78. The extent of projection by the detents 120 and the lips 122 is sufficient that the side members 90 and 92 cannot be pivoted about their pivotal axes 100 and 102 respectively without causing contact between the lip 122 and an adjacent detent 120. As such, the side members 90 and 92 cannot pivot from their slide-holding position to their slide-releasing position unless the side members 90 and 92 are forcibly moved beyond the point of contact between the detent 120 and the lip 122. Since the side members 90 and 92 as well as the end members 76 and 78 are made of a somewhat flexible material and the pivotal connection between these members is itself somewhat loose, the side members 90 and 92 can be forced to the slide-releasing position shown in FIGS. 4 and 5. However, so long as the side members 90 and 92 are disposed at their slide-holding position, the slides 94 will not fall from the slide holder 16 because the side members 90 and 92 cannot by themselves pivot to the slide-releasing position. As such, accidental spilling of slides 94 from the slide holder 16 is avoided.

As indicated earlier, the side members 90 and 92 are preferably made of cellulose acetate butyrate or other similar material. This material is particularly advantageous not only because it is transparent but also because it can be easily molded thereby permitting each of the side members 90 or 92 to be made in one piece by a simple process. The side member 90, as best viewed in FIGS. 3 and 5, is molded with a plurality of inwardly projecting bodies indicated generally at 105 presenting an inwardly facing rectangular area and vertically disposed sides between adjacent bodies 104. Disposed between adjacent inwardly projecting bodies 105 is an inwardly projecting area, shown generally at 107, which has a vertically aligned angular cross section. Since the area 105 are separated by an area 107, a slot 110 is produced for receiving the ends of a slide 94. This slot 110 is vertically arranged and disposed perpendicular to the pivot axis of each side member so as to support slides 94 with their major side surfaces oriented in a substantially vertical direction when the slides 94 are in position for water quality monitoring.

Referring again to FIG. 3, the side member 90 is pivoted to the end member 72 by a rivot or the like 112 preferably made of nylon and which passes through both the end member 72 and the side member 90. This type of pivotal connection is employed at opposite ends of both side members 90 and 92. While nylon rivots are preferably used to provide a pivotal connection between the side members 90 and 92 and the end members 76 and 78, it will be recognized by those skilled in the art that other forms of pivotal connection can be utilized equally effectively.

Referring now to FIGS. 4 and 5, the slide holder 16 is shown with each of the side members 90 and 92 disposed at its slide-releasing position whereat each slide 94 can be grasped, for example, at the corners 114, and raised vertically out of the slide holder 16. Similarly, clean slides 94 may be placed into the slide holder 16 when both side members 90 and 92 are disposed at their slide-releasing position as shown in FIGS. 4 and 5.

Once the slide holder 16 has been loaded with fresh slides 94, the side members 90 and 92 of the slide holder 16 are forcefully pivoted about their respective pivot axes 100 and 102 by simply pressing downwardly on the top of the slides 94 in a direction indicated by the arrow labeled 119 in FIG. 4. When this occurs, the inwardmost disposed ends of each side member 90 and 92 will swing in a direction indicated generally by the arrows 123 and 124. As this occurs, the upper portion of each side member 90 and 92 swings inwardly in a direction indicated respectively by the arrows labeled 126 and 128. Eventually, the side members 90 and 92 will pivot to their slide-engaging position as depicted in FIGS. 1, 2 and 6. As such, slides 94 can easily be removed from the slide holder 16 by first forcefully pivoting the side members 90 and 92 by hand to their slide-releasing position as shown in FIGS. 4 and 5. The slides are easily grasped and removed. Once new slides 94 have been placed into the slide holder 16, by pressing downwardly on the top of each of the slides in the direction indicated by the arrow 119, the side members pivot back to their slide-holding position.

From the foregoing description, it is clear that the preferred embodiment of the present invention provides a periphyton sampler for water quality monitoring which includes a slide holder 16 holding a plurality of slides 94. The slide holder 16 in use is positioned on a bail 19 so that each of the slides 94 is arranged with its principal surface areas disposed substantially vertical to the water surface. Since the slide holder 16 is disposed away from the pivot axis of the bail 18 through each of the floatation members 12 and 14, the slide holder 16, even if the sampler were in use turned over so that the holder 16 is above the water surface, the holder 16 will pivot about the pivot axis through the floatation members 12 and 14 so as to be again disposed below the water surface 38 as viewed in FIG. 2. As such, the bail 18 shape assures that the slide holder 16 will not be directly exposed for prolonged periods of time to the air and direct sunlight.

Furthermore, by reason of the fact that the bail 18 is disposed along the symmetry axis of each of the floatation members 12 and 14, there are no uneven forces on the floatation members 12 and 14, and therefore, they tend to remain substantially flat with respect to the water surface. Also, since each floatation members 12 and 14 is individually pivoted to the bail 18, they can move independently of each other. As such, wave action on the floatation members 12 and 14 does not contribute to a tendancy of the sampler 10 capsize.

By selecting the size of the floatation members 12 and 14, the buoyance of the floatation members 12 and 14 can be adjusted so that only the desired amount of each floatation members 12 and 14 will extend upwardly above the water surface when the sampler is in actual use. As such, visibility of the sampler in use is reduced thereby reducing the likelihood of vandalism.

Since the sampler 10 of the present invention uses a slide holder 16 which is removable from the bail 18 once the retainer clip 20 has been disconnected, a slide holder 16 can be preloaded at a laboratory for quick and easy installation into a sampler 10 at the actual location of the sampler. The pivotal construction of the slide holder 16 permits easy insertion or removal of slides 94 therefrom once the holder 16 has been removed from the bail 18. The detent 120 and lip 122 arrangement assures the holder 16, once loaded with slides, will not accidently open.

While the foregoing description has been made with particular emphasis on a preferred embodiment of the invention, it will be readily recognized by those of skill in the art that numerous modifications in form only may be made without departing from the spirit and scope of the invention as defined more particularly by the following claims.

What is claim is:

1. A periphyton sampler for water quality monitoring comprising, in combination:
    a pair of floatation members for floating the sampler in water;
    a bail pivotally connected to said floatation members on a pivot axis passing through said members for connecting and also separating both said floatation members;
    a slide holder adapted to hold a plurality of slides, said slide holder having a slide-holding position whereat slides are securely held thereby and a slide-releasing position whereat slides are easily removed from said slide holder; and
    the portion of said bail located between said floatation members being operative with said slide holder to support said slide holder below said pivot axis so that said slide holder will sink below the water surface whenever the sampler is immersed in water.

2. The periphyton sampler of claim 1 wherein said slide holder is removable from the portion of said bail between said floatation members.

3. The periphyton sampler of claim 2 wherein said slide holder comprises:
    a pair of end members positioned in spaced relation to each other;
    a pair of side members each pivoted to both said end members at opposite ends of each side member, said side members being pivoted between said slide-holding position and said slide-releasing position.

4. The periphyton sampler of claim 3 wherein each said side member has a plurality of slide-receiving slots each for receiving a slide therein so as to space each slide from other slides supported by said slide holder.

5. The periphyton sampler of claim 3 wherein each said side member has a generally channel-shaped cross section along the longitudinal axis thereof which extends between said end members, the opposite ends of each said slide projecting into the channel provided by each said side member when disposed at said slide-holding position to prevent any slide from falling out of said slide holder.

6. The periphyton sampler of claim 5 additionally including a releasable locking means for securing said slide holder to said bail.

7. The periphyton sampler of claim 3 additionally including means to prevent said side members to freely pivot from their slide-holding position to their slide-releasing position but permitting forceful pivoting of the side members from their slide-holding position to their slide-releasing position so as to avoid accidental spilling of slices from said slide holder.

8. The periphyton sampler of claim 2 wherein said slide holder includes guides alignable with said bail, said guides being located near the center of balance of said slide holder so that the sampler will in use be balanced to maintain each slide in the same attitude and at substantially the same distance from the water surface.

9. The periphyton sampler of claim 1 wherein said slide holder is made of transparent material so that slides held thereby will not be shaded during water quality monitoring.

10. The periphyton sampler of claim 1 wherein said floatation members are of a color which is not easily seen while the sampler is in water to reduce the likelihood of tampering.

11. The periphyton sampler of claim 1 wherein said floatation members are of a size and shape so that no more than one half of each floatation member in use is above the water surface to reduce the likelihood of tampering.

12. The periphyton sampler of claim 1 wherein said slide holder is shaped so that each slide held thereby is maintained at substantially the same attitude in use with respect to the water surface as each other slide.

13. The periphyton sampler of claim 1 wherein said slide holder is positioned on said bail and shaped so that each said slide held thereby is, in use, disposed substantially the same distance from the surface of the water.

14. The periphyton sampler of claim 1 additionally including at least one anchor point for conveniently attaching a securing line to hold the sampler in substantially one position in moving water.

15. The periphyton sampler of claim 1 additionally including at least one anchor point permitting the sampler in use to be anchored by a line to a secure point below the water surface.

16. A periphyton sampler for water quality monitoring comprising, in combination:
a pair of floatation members for floating the sampler in water;
a bail pivotally connected to said floatation members on a pivot axis passing through said members along an axis of symmetry thereof for connecting and separating both said floatation members; and
a slide holder adapted to hold a plurality of slides, said slide holder including two spaced side members pivotal between a slide-holding position whereat slides are securely held between said side members and a slide-releasing position whereat slides are easily removed from the slide holder, said slide holder being attached to said bail between said floatation members in a manner so that the center of gravity of said slide holder and said bail is disposed below said pivot axis.

17. A slide holder for a periphyton sampler including floatation means and a bail pivotally connected to said floatation means, said slide holder comprising, in combination:
at least one support member; and
a pair of elongated side members each being channel shaped in cross section transverse to the longitudinal axis of said side member, said side members each being pivotally attached to each said support member and pivotal between a slide-holding position whereat said side members are disposed with the opening provided by the channel of each said side member facing toward the other said opening, each said opening providing means for receiving the ends of a slide, and a slide-releasing position whereat said opening of said side members are angularly disposed relative to each other so that slides can be easily inserted or removed from between said side members, said side members including means for receiving at least a portion of said bail such that said slide holder is supportable by said bail below the water surface when said sampler is immersed in water.

18. The slide holder of claim 17 additionally including a plurality of slide-receiving slots disposed in spaced relation along the longitudinal axis of each said side member, each said slot being adapted to receive the end of a slide.

19. The slide holder of claim 18 wherein each said slide-receiving slot is shaped to receive the end of a slide when the slide holder is disposed either at said slide-holding position or said slide-releasing position thereby facilitating loading and unloading said slide holder.

20. The slide holder of claim 19 wherein said slide-receiving slots are formed by two inwardly projecting bodies with opposed substantially parallel planar surfaces for receiving therebetween the ends of a slide and additionally including an inwardly projecting body disposed between said two planar surfaces, said inwardly projecting body between said planar surfaces being shaped to substantially prevent longitudinal movement of a slide in said slide holder but permitting pivoting of said side members between said slide-holding position and said slide-releasing position while a slide is positioned in said holder.

21. The slide holder of claim 17 additionally including:
a locking mechanism for holding said side members at their slide-holding position to thereby prevent accidental pivoting of said side members to their slide-releasing position.

22. The slide holder of claim 17 wherein said support means comprises a pair of end members disposed at opposite ends of each said slide member.

23. The slide holder of claim 22 additionally including locking means to prevent accidental pivoting of said side members from their slide-holding position to their slide-releasing position but permitting deliberate pivoting of said side members from their slide-holding to their slide-releasing position.

24. The slide holder of claim 22 additionally including at least one detent disposed on each said end member between said end member and each said side member and a lip on each said side member adjacent each said end member, said lip being operative in cooperation with the adjacent detent to prevent accidental pivoting of said side member from said slide-holding position to said slide-releasing position unless pivotal force is directly applied to said side members to thereby deliberately pivot said side members from their slide-holding position to their slide-releasing position.

25. A periphyton sampler for water quality monitoring comprising, in combination:
   a pair of floatation members for floating the sampler in water;
   a bail for pivotally connecting and separating both said floatation members, said pivotal connection between said bail and each said floatation members being disposed along an axis of symmetry of each said floatation member;
   a slide holder adapted to hold a plurality of slides; and
   means for supporting said slide holder from said bail at a location between said floatation members.

26. The periphyton sampler of claim 25 wherein said slide holder is removable from said slide holder.

27. The periphyton sampler of claim 25 wherein said floatation members are of a color not easily seen while the sampler is in water to reduce the likelihood of tampering.

28. The periphyton sampler of claim 25 wherein said floatation members are of a size and shape so that no more than one half of each floatation member, in use, is above the water surface to reduce the likelihood of tampering.

29. The periphyton sampler of claim 25 wherein said slide holder includes a pair of elongated side members each being channel-shaped in cross section transverse to the longitudinal axis of said side member, said side members being pivotal between a slide-holding position whereat said side members are disposed with the opening provided by the channel of each said side member facing toward the other opening, each said opening providing means for receiving the ends of a slide, and a slide-releasing position whereat said openings of said side members are angularly disposed relative to each other so that slides can be easily inserted or removed from between said side members.

30. The periphyton sampler of claim 29 wherein each said side member includes a plurality of slide-receiving slots each to receive the end of a slide and position each slide in spaced relation to the other received slides.

* * * * *

UNITED STATES PATENT AND TRADEMARK OFFICE
CERTIFICATE OF CORRECTION

PATENT NO. : 3,955,421

DATED : May 11, 1976

INVENTOR(S) : Robert J. Doernberg; Earl J. Huddleston; James F. Mariol

It is certified that error appears in the above-identified patent and that said Letters Patent are hereby corrected as shown below:

Col. 2, line 1, after "first" delete -- and --

Col. 5, line 62, "is" should be -- in --

Col. 7, line 56, "19" should be -- 18 --

Claim 7, line 7, "slices" should be -- slides --

Claim 20, line 1, "Claim 19" should be --Claim 18 --

Claim 22, line 3, "slide" should be -- side --

Signed and Sealed this

Thirty-first Day of August 1976

[SEAL]

Attest:

RUTH C. MASON
*Attesting Officer*

C. MARSHALL DANN
*Commissioner of Patents and Trademarks*